United States Patent [19]

Yamada et al.

[11] Patent Number: 5,264,568

[45] Date of Patent: Nov. 23, 1993

[54] PROCESS FOR PREPARING PYRODEXTRIN HYDROLYZATE BY ENZYMATIC HYDROLYSIS

[75] Inventors: Koji Yamada, Nishinomiya; Isao Matsuda, Itami, both of Japan

[73] Assignee: Matsutani Chemical Industries Co., Ltd., Hyogo, Japan

[21] Appl. No.: 814,353

[22] Filed: Dec. 27, 1991

[30] Foreign Application Priority Data

May 27, 1991 [JP] Japan .................................. 152334

[51] Int. Cl.$^5$ ...................... C08B 30/12; C08B 37/16
[52] U.S. Cl. .................................. 536/103; 536/124; 127/32; 127/67; 127/70; 127/71
[58] Field of Search ................ 536/103, 124, 1.1; 127/32, 67, 70, 71

[56] References Cited

U.S. PATENT DOCUMENTS 3,086,008  4/1963  Opila et al. ........................... 536/103
3,974,032  8/1976  Harjes et al. ......................... 426/658
4,668,626  5/1987  Kobayashi et al. .................... 435/95
4,782,143  11/1988 Morehouse et al. .................. 435/202
5,139,575  8/1992  Matsuda et al. ..................... 127/23

OTHER PUBLICATIONS

DATABASE WPIL Week 1788, Dervent Publications Ltd., London, GB; AN 88-117484.
Abstract No. 126603z, Chemical Abstracts, vol. 97, No. 15, Columbus, Ohio.

Primary Examiner—Nathan M. Nutter
Attorney, Agent, or Firm—Sughrue, Mion, Zinn, Macpeak & Seas

[57] ABSTRACT

A process comprising dissolving a pyrodextrin in water, hydrolyzing the solution with alpha-amylase at a low temperature to obtain a hydrolyzate of reduced viscosity, further hydrolyzing the hydrolyzate to an intermediate extent at a high temperature, autoclaving the resulting hydrolyzate, finally hydrolyzing the hydrolyzate with alpha-amylase again after cooling, and autoclaving the final hydrolyzate again. Pyrodextrin hydrolyzate can be prepared without impairing the inherent characteristics of pyrodextrin.

4 Claims, No Drawings

PROCESS FOR PREPARING PYRODEXTRIN HYDROLYZATE BY ENZYMATIC HYDROLYSIS

BACKGROUND OF THE INVENTION

1. Field of the Invention

The present invention relates to a process for hydrolyzing pyrodextrin with alpha-amylase derived from *Bacillus licheniformis* to prepare a pyrodextrin hydrolyzate.

2. Description of the Prior Art

U.S. Pat. No. 2,965,520 discloses a process for hydrolyzing (liquefying) starches with alpha-amylase, i.e., a process comprising hydrolyzing a starch slurry with an acid, adjusting the resulting hydrolyzate to a pH of 4 to 10, and adding alphaamylase (not comprising the amylase produced from *B. licheniformis*) for further hydrolysis to prepare a product with greater stability.

U.S. Pat. No. 3,249,512 discloses a process wherein a suspension of crude starch is hydrolyzed with alpha-amylase free from protease (and not comprising the amylase produced from *B. licheniformis*) at a pH of 6.5 to 7.5 and subsequently heated to 99° C. to inactivate the alpha-amylase and to obtain a hydrolyzate of improved taste.

U.S. Pat. No. 3,378,462 discloses a process comprising adding a calcium salt and sodium salt to a starch slurry, adding bacterial alpha-amylase (not comprising the amylase produced from *B. licheniformis*) to the suspension at a pH of 5.5 to 7.7, and heating the mixture at 77° to 93° C. for hydrolysis to obtain a hydrolyzate of high DE.

U.S. Pat. Nos. 3,695,933, No. 3,756,853 and No. 3,756,919 disclose a process wherein a starch slurry having a concentration of up to 50% is hydrolyzed with bacterial alpha-amylase (not comprising the amylase produced from *B. licheniformis*) at a pH of 6.5 to 8.0 at 80° to 95° C., and a two-step liquefaction process using amylase which comprises this process and wherein the hydrolyzate obtained by the process is heated to 150° C., then cooled to 80° to 90° C. and hydrolyzed again with the addition of bacterial alpha-amylase. The two-step process, which is similar to the process of U.S. Pat. No. 2,965,520, is adapted to achieve an improved filtration rate.

U.S. Pat. No. 3,849,194 discloses a process for preparing a starch hydrolyzate 5 to 20 in DE and non-hazing by adding bacterial alpha-amylase (not comprising the amylase produced from *B. licheniformis*) to a waxy starch slurry at a pH of 6 to 8 to effect hydrolysis approximately to DE 5 at a temperature of at least 85° C., and subsequently lowering the temperature below 80° C. without heat-treatment to effect further hydrolysis.

U.S. Pat. No. 3,853,706 discloses a process comprising adding bacterial alpha-amylase (not comprising the amylase produced from *B. licheniformis*) to a slurry of nonwaxy starch having a concentration of up to 40%, hydrolyzing the suspension to DE 2 to 15 at a temperature of up to 95° C., heating the hydrolyzate above 95° C., then cooling the hydrolyzate to below 85° C., and further hydrolyzing the hydrolyzate to DE 5 to 20 with addition of bacterial alpha-amylase to obtain a nonhazing syrup.

U.S. Pat. No. 3,910,820 discloses a process wherein a slurry of crude starch is heated at 50 to 60° C. for 1 to 5 hours as a pretreatment before the addition of alpha-amylase for hydrolysis, then hydrolyzed with alpha-amylase (not comprising the amylase produced from *B. licheniformis*) at 80 to 105° C., subsequently cooled to 70° to 85° C. without heat-treatment, and thereafter hydrolyzed with an additional amount of alpha-amylase to obtain a hydrolyzate which is easy to refine.

U.S. Pat. No. 3,912,590 discloses a short time hydrolysis process wherein a stach slurry having a concentration of at least 25% is hydrolyzed at 100° to 115° C. for 1 to 60 minutes with alpha-amylase produced from *B. licheniformis*, followed by cooling to 80° to 100° C. and hydrolyzed to at least DE 12 without heat-treatment and without using an additional amount of alpha-amylase.

U.S. Pat. No. 4,298,400 discloses a process wherein a slurry of nonwaxy starch is hydrolyzed with alpha-amylase produced from *Bacillus subtilis* or *Bacillus mesentericus* at a pH of 7.5 to 8 at 90° to 92° C. to below DE 15, followed by heating to 150° C., then cooling to 80° to 85° C. and thereafter hydrolyzed to DE 5 to 20 with an additional amount of alpha-amylase to obtain a nonhazing syrup.

U.S. Pat. No. 4,410,368 discloses a process comprising of adding a carbonate (pH buffer) to a starch slurry having a concentration of 15 to 30% to adjust the suspension to a pH of 6 to 8, adding heat-resistant bacterial alpha-amylase (produced from *B. licheniformis*) to the slurry, heating the slurry to 100° to 110° C. over a period of 5 to 15 minutes to effect hydrolysis, then heating the hydrolyzate at 140° to 150° C. for 15 to 40 minutes, subsequently cooling the hydrolyzate to 95° to 100° C., hydrolyzing the hydrolyzate with an additional amount of alpha-amylase for 5 to 30 minutes approximately to DE 2, and further adding beta-amylase to the resulting hydrolyzate for saccharification to obtain a hydrolyzate suitable for preparing maltose.

U.S. Pat. Nos. 4,684,410, No. 4,689,088, No. 4,699,669 and No. 4,699,670 disclose a process comprising hydrolyzing a starch slurry with an acid or enzyme up to DE 3, adding bacterial alpha-amylase to the hydrolyzate at a pH of 6.5 to 8 and effecting hydrolysis at 95° to 100° C. to obtain a hydrolyzate which can be filtered with an improved rate.

U.S. Pat. No. 4,933,279 discloses a process comprising adding a mixture of bacterial alpha-amylases produced from *B. licheniformis* and *Bacillus stearothermophilus* to a slurry of starch or starchy grains at a pH of 5.5 to 6.2, hydrolyzing the slurry at 100° to 115° C. for 1 to 60 minutes, and cooling the hydrolyzate to 90° to 100° C. without heat treatment, followed by hydrolysis for 30 to 180 minutes to obtain a hydrolyzate with elimination of any problem of sediment.

With respect to the enzymatic hydrolysis of pyrodextrin, nothing has been reported except that B. Brimhall, Ind. Eng. Chem., 36, 72(1944) states that when British gum prepared by heating starch without adding any acid thereto is hydrolyzed with alpha-amylase (not comprising the amylase produced from *B. licheniformis*), the limit of decomposition is 3.5% calculated as maltose, i.e., about 7.4 calculated as DE.

However, these processes are hydrolysis (liqueiaction) processes for starch, crude starch or pyrodextrin prepared without the addition of acid, with any of these processes encountering difficulties when used for hydrolyzing pyrodextrin of the type mentioned, and are not suited to practice for this purpose. Stated more specifically, when water is added to starch, particles of starch become suspended in water to form a starch slurry without dissolving in water, whereas if water is added to pyrodextrin, pyrodextrin dissolves in water to make a highly viscous solution. Accordingly, when pyrodextrin is dissolved in water to a usual hydrolyzing concentration of 30 to 45% in the first step for the enzymatic hydrolysis of pyrodextrin, the solution becomes highly viscous and difficult to prepare, while the solution, if prepared, is difficult to stir and to transport by pumping for transfer to the subsequent process. Additionally, the acid used for the preparation of pyrodextrin reacts with the protein, oil and fat present in starch during heating to form impurities, which are extremely difficult to remove for purification since some of them are combined with starch. These impurities remain even after the hydrolyzate has been decolorized, filtered and desalted with ion exchange resin, rendering the product non-transparent and permitting the product to contain many colored substances. In the case where the product is used for foods, pharmaceuticals and industrial applications which are the main uses of pyrodextrin, such impurities are prone to react with various other components, and are likely to produce precipitates during or after the production of food or the like, hence a serious drawback. Further the hydrolysis process wherein an acid is used has the defect that the characteristic decomposition mechanism of the acid is liable to impair the inherent properties of pyrodextrin.

SUMMARY OF THE INVENTION

During continued research we have heretofore conducted, we conceived a novel idea of preparing pyrodextrin hydrolyzate for use in a wider variety of foods. To realize this idea, we started research on the use of pyrodextrin of high viscosity at high concentrations, improvements in the filterability and transparency of hydrolyzates and reduction of precipitates and colored substances to develop a process for preparing pyrodextrin hydrolyzate of high purity.

Accordingly, the main object of the present invention is to develop a process for preparing a pyrodextrin hydrolyzate free of the foregoing drawbacks to be involved in hydrolyzing pyrodextrin with alpha-amylase, in refining the hydrolyzate and in the quality of the product.

This object can be fulfilled basically by a process which comprises dissolving a pyrodextrin in water, hydrolyzing the solution with alpha-amylase at a low temperature to obtain a hydrolyzate of reduced viscosity, further hydrolyzing the hydrolyzate to an intermediate extent at a high temperature, autoclaving the resulting hydrolyzate, finally hydrolyzinq the hydrolyzate with alpha-amylase again after cooling, and autoclaving the final hydrolyzate again.

DETAILED DESCRIPTION OF THE INVENTION

The pyrodextrin to be used as the starting material of the present invention is prepared by adding an acid to starch and heat-treating the starch in a state in which the starch contains up to 20% of water. Pyrodextrins as such are those containing at least 95% of soluble portions when dissolved in water at 20° C. at a concentration of 1%.

Any of these pyrodextrins are usable as the starting material of the invention. When the pyrodextrin is prepared by heating acid-added starch at a high temperature or for a prolonged period of time, the starch, and the proteins and oils or fats present in the starch react with one another to form substances which will be difficult to remove for refining, or such components themselves will be difficult to remove, whereas the present process can be practiced free of such difficulties.

The alpha-amylase for use as a hydrolyzing enzyme in the present invention is limited only to the one produced from *B. licheniiormis*. TERMAMYL, a heat-stable carbohydrase produced by a selected strain of *Bacillus licheniformis*, (product of Novo Industry Co., Ltd.) is advantageously usable as a commercial product.

Briefly stated, the process of the present invention is as follows.

Pyrodextrin, prepared from acid-added starch and soluble in cold water, is dissolved in water to a concentration of 20 to 45%, and the solution is adjusted to a pH of 7.0 to 8.5 and thereafter maintained at a temperature of 20° to 40° C. for 6 to 20 hours (this treatment will hereinafter be referred to as the "primary hydrolysis"). Next, the solution is adjusted to a pH of 5.5 to 6.5, about 0.05 to about 0.2% of alpha-amylase is thereafter added to the solution based on the solids thereof, and the solution is then heated to a temperature of 80° to 90° C. and hydrolyzed to 30 to 60% of the DE value desired for the final product while maintaining the solution at the same temperature (this treatment will hereinafter be referred to as the "secondary hydrolysis"). The hydrolyzate is adjusted to a pH of 4.0 to 5.0, autoclaved at 115° to 135° C. for 3 to 10 minutes (this treatment will hereinafter be referred to as the "primary autoclaving"), cooled to 80° to 90° C. and then adjusted to the same pH when required. About 0.05 to about 0.2% of the same enzyme is added again to the hydrolyzate, which is thereafter hydrolyzed similarly to the desired DE (this treatment will hereinafter be referred to as the "tertiary hydrolysis"). The resulting hydrolyzate is adjusted to a pH of 4.0 to 5.0 and then autoclaved under the same condition as above (this treatment will hereinafter be referred to as the "secondary autoclaving") to complete hydrolysis. The amount of alpha-amylase is not limited to the above-mentioned amount; an amount equivalent to the above may be used in accordance with the activity of alpha-amylase. The time required for hydrolysis is controllable by varying the amount of enzyme used. Subsequently, the hydrolyzate is cooled to about 80° C., and thereafter decolorized with activated carbon, filtered, and desalted and decolorized with ion exchange resin.

The process of the present invention is a novel hydrolysis process characterized by the combination of three-step liquefaction and two-step autoclaving, assuring smooth transport of solutions or hydrolyzates and facilitated procedures for neutralization and for decolorization, filtration, desalting and like refining processes, and giving a pyrodextrin hydrolyzate which is excellent in transparency, reduced in the contents of colored substances and less likely to permit formation of precipitates.

To clarify the features of the present invention, experimental examples will be described below in detail.

EXPERIMENTAL EXAMPLES

Preparation of Material Pyrodextrin

To 1,000 kg of commercial corn starch, placed in U a ribbon mixer was sprayed 75 liters of 1% hydrochloric acid solution with stirring. The starch and the solution were then uniformly mixed together by a disintegrator, and the mixture was aged for 5 hours in the ribbon mixer again. The mixture was pre-dried to a water content of about 3% by a flash dryer and thereafter heated in a rotary kiln at 150° C. for 4 hours to obtain about 800 kg of pyrodextrin.

Basic Conditions for Experiments

The material, i.e., the pyrodextrin prepared above, was made into a 40% aqueous solution, which was treated under the conditions listed in Table 1, with some of the conditions altered in each experiment. As to the condition not mentioned in each of the experimental examples to follow, the corresponding condition given in Table 1 was used. For pH adjustment, 1N aqueous solution of sodium hydroxide was used. The alpha-amylase used was TERMAMYL 120 L (product of Novo Industry Co., Ltd.) commercially available. The hydrolyzate was decolorized at 70° C. for 30 minutes with activated carbon added thereto in an amount of 1% based on the solids of the hydrolyzate, then filtered, decolorized and desalted with a mixed-bed ion exchange resin, and concentrated to a concentration of 30% in vacuo. A portion of the concentrate was diluted to a concentration of 10%. The concentrate and the dilution were used for analysis and testing.

The rate of filtration was expressed in terms of the amount of filtrate per minute which was determined by adjusting the hydrolyzate to a concentration of 30%, adding activated carbon to a 500 ml portion of the adjusted hydrolyzate in an amount of 1% based on the solids thereof to decolorize the hydrolyzate at 70° C. for 30 minutes, filtering the resulting hydrolyzate in vacuo with filter paper having a diameter of 10 cm and precoated with kieselguhr, and measuring the time required for filtering the whole amount of the hydrolyzate. The turbidity was expressed in terms of the absorbancy, at a wavelength of 720 nm, of the 10% dilution of the refined concentrate, as measured using a colorimeter and a 10 cm cell.

The amount of precipitate produced was determined by adding to a commercial orange juice (100% orange juice, product of DOLE CO.) the refined concentrate in an amount, calculated as solids, corresponding to 5% of the quantity of the juice, pouring the mixture into graduated test tubes, 2 cm in diameter and 20 cm in length, in an amount of 50 ml in each tube, allowing the test tubes to stand in a refrigerator at 4° C. for 10 days, thereafter measuring the amount of resulting precipitate with reference to the scale, and calculating the combined amount, in percentage, of the precipitate based on the whole amount of the mixture. When required, the DE of the purified concentrate was measured by the Willstätter-Schudel method.

TABLE 1

| Treatment | Condition | | |
|---|---|---|---|
| | pH | Dosage of α-amylase (%) | Temp (°C.) | Time (min) |
| Primary hydrolysis | 7.5 | 0.2 | 30 | 720 |
| Secondary hydrolysis | 6.0 | — | 85 | 25 |
| Primary autoclaving | 4.5 | — | 125 | 10 |
| Tertiary hydrolysis | 6.0 | 0.1 | 85 | 30 |
| Secondary autoclaving | 4.5 | — | 125 | 10 |

EXPERIMENTAL EXAMPLE 1

Primary Hydrolysis Temperature and Time Vs. Amount of Precipitate Produced

The material solution was treated under the conditions listed in Table 1, except that the solution was subjected to primary hydrolysis at varying temperatures for varying periods of time. The refined concentrates obtained were tested for the amount of precipitate produced. Table 2 shows the result.

TABLE 2

| Temp | Time | | | | | |
|---|---|---|---|---|---|---|
| | 4 | 6 | 8 | 12 | 18 | 24 |
| 20 | 13.0 | 10.0 | 9.4 | 8.2 | 7.2 | 5.6 |
| 25 | 10.4 | 7.2 | 6.0 | 5.6 | 4.0 | 3.4 |
| 30 | 5.4 | 3.8 | 3.4 | 2.6 | 2.4 | 2.6 |
| 40 | 4.6 | 3.0 | 3.0 | 2.4 | 2.2 | 2.2 |
| 45 | 5.0 | 4.0 | 3.6 | 3.8 | 3.4 | 3.2 |
| 50 | 8.4 | 8.2 | 7.8 | 8.0 | 7.4 | 8.0 |

EXPERIMENTAL EXAMPLE 2

Primary Hydrolysis pH and Temperature Vs. Amount of Precipitate Produced

The material solution was treated under the conditions listed in Table 1, except that the solution was adjusted to varying pH values and subjected to primary hydrolysis for varying periods of time. The refined concentrates obtained were similarly tested to determine the amount of precipitate produced. Table 3 shows the result.

TABLE 3

| pH | Temp. | | | | | |
|---|---|---|---|---|---|---|
| | 20° C. | 25° C. | 30° C. | 40° C. | 45° C. | 50° C. |
| 6.0 | 12.8 | 12.0 | 11.0 | 9.2 | 10.4 | 13.0 |
| 6.5 | 12.0 | 7.4 | 6.6 | 6.0 | 6.6 | 7.4 |
| 7.0 | 11.6 | 3.0 | 2.8 | 2.8 | 3.4 | 8.6 |
| 7.5 | 8.8 | 2.6 | 2.6 | 2.4 | 3.8 | 8.0 |
| 8.0 | 7.4 | 2.6 | 2.4 | 2.0 | 2.6 | 7.2 |
| 8.5 | 7.2 | 2.8 | 2.8 | 2.6 | 3.2 | 8.8 |
| 9.0 | 8.4 | 7.8 | 7.6 | 8.2 | 9.0 | 11.4 |

Tables 2 and 3 reveal that an increased amount of precipitate resulted if the temperature was below 25° C. or above 45° C., the pH was lower than 7.0 or higher than 8.5, or the hydrolysis time was less than 6 hours. Most preferably, therefore, the pH is 7.0 to 8.5, the temperature is 25° to 40° C. and the time is at least 6 hours.

EXPERIMENTAL EXAMPLE 3

Secondary Hydrolysis Vs. Degree of Coloration and DE

The material solution was treated under the conditions listed in Table 1, except that the hydrolyzate resulting from the primary hydrolysis was adjusted to varying pH values, then heated to varying temperatures and thereafter subjected to secondary hydrolysis. The refined concentrates obtained were checked for the degree of coloration and DE. The results are given in Table 4 and Table 5.

TABLE 4

| pH | Temp. | | | | | |
|---|---|---|---|---|---|---|
| | 75° C. | 80° C. | 85° C. | 90° C. | 95° C. | 100° C. |
| 5.0 | 0.81 | 0.95 | 0.90 | 1.04 | 1.27 | 1.48 |

TABLE 4-continued

| pH | 75° C. | 80° C. | 85° C. | 90° C. | 95° C. | 100° C. |
|---|---|---|---|---|---|---|
| 5.5 | 0.96 | 1.13 | 1.08 | 1.22 | 1.49 | 1.82 |
| 6.0 | 0.97 | 1.41 | 1.11 | 1.24 | 1.61 | 1.95 |
| 6.5 | 1.13 | 1.44 | 1.38 | 1.47 | 1.87 | 2.32 |
| 7.0 | 1.25 | 1.48 | 1.52 | 1.63 | 2.14 | 2.49 |
| 7.5 | 1.46 | 1.57 | 1.64 | 1.94 | 2.46 | 2.86 |

TABLE 5

| pH | 75° C. | 80° C. | 85° C. | 90° C. | 95° C. | 100° C. |
|---|---|---|---|---|---|---|
| 5.0 | 5.32 | 7.75 | 7.83 | 8.32 | 8.47 | 8.53 |
| 5.5 | 5.42 | 7.84 | 7.93 | 8.51 | 8.63 | 8.71 |
| 6.0 | 5.66 | 8.06 | 8.10 | 8.52 | 8.71 | 8.77 |
| 6.5 | 5.83 | 8.11 | 8.22 | 8.64 | 8.80 | 8.85 |
| 7.0 | 5.94 | 8.14 | 8.24 | 8.72 | 8.83 | 8.92 |
| 7.5 | 6.12 | 8.18 | 8.30 | 8.80 | 8.92 | 8.98 | pH values not lower than 7 or temperatures not lower than 95° C. are not suitable, since marked coloration resulted. When the pH was not higher than 5 or the temperature was up to 75° C., remarkable coloration was observed, whereas the DE value then determined indicated a low hydrolysis velocity. Most preferably, therefore, the pH is 5.5 to 6.5, and the temperature is 80° to 90° C.

EXPERIMENTAL EXAMPLE 4

Primary Autoclaving Temperature and Time Vs. Turbidity

The material solution was treated under the conditions listed in Table 1, except that the hydrolyzate resulting from the secondary hydrolysis was primarily autoclaved at varying temperatures for varying periods of time. The turbidity of the refined concentrates was determined with the result given in Table 6.

TABLE 6

| time | 105° C. | 115° C. | 125° C. | 135° C. | 140° C. | 150° C. |
|---|---|---|---|---|---|---|
| 1 min. | 0.126 | 0.085 | 0.060 | 0.041 | 0.029 | 0.025 |
| 3 | 0.104 | 0.032 | 0.025 | 0.024 | 0.025 | 0.024 |
| 5 | 0.089 | 0.029 | 0.025 | 0.020 | 0.020 | 0.020 |
| 10 | 0.074 | 0.027 | 0.020 | 0.018 | 0.016 | 0.017 |
| 15 | 0.051 | 0.025 | 0.018 | 0.018 | 0.015 | 0.018 |
| 20 | 0.054 | 0.021 | 0.019 | 0.017 | 0.013 | 0.017 |

EXPERIMENTAL EXAMPLE 5

Primary Autoclaving pH and Temperature Vs. Degree of Coloration

The material solution was treated under the conditions listed in Table 1, except that the hydrolyzate resulting from the secondary hydrolysis was adjusted to varying pH values and then primarily autoclaved at varying temperatures. The refined concentrates obtained were checked for the degree of coloration. Table 7 shows the result.

TABLE 7

| pH | 105° C. | 115° C. | 125° C. | 135° C. | 140° C. | 150° C. |
|---|---|---|---|---|---|---|
| 3.5 | 0.75 | 0.94 | 1.10 | 1.23 | 1.44 | 1.36 |
| 4.0 | 0.72 | 0.94 | 1.03 | 1.28 | 1.34 | 1.42 |
| 5.0 | 0.78 | 0.96 | 1.18 | 1.39 | 1.46 | 1.41 |
| 5.5 | 1.06 | 1.35 | 1.37 | 1.72 | 1.86 | 1.84 |

TABLE 7-continued

| pH | 105° C. | 115° C. | 125° C. | 135° C. | 140° C. | 150° C. |
|---|---|---|---|---|---|---|
| 6.0 | 1.28 | 1.39 | 1.54 | 2.05 | 2.23 | 2.44 |

Tables 6 and 7, showing the conditions for the primary autoclaving and the result obtained, indicate the following. The turbity was high when the temperature was lower than 115° C., remained unchanged at temperatures above 140° C., was high when the time was 1 minute, or remained unchanged when the time was over 10 minutes. The degree of coloration remained unchanged when the pH was below 4, or markedly increased at pH values above 5.0 or at temperatures of not lower than 140° C. Accordingly, the optimal conditions for primary autoclaving are 115° to 135° C. in temperature, 4.0 to 5.0 in pH and 3 to 10 minutes in time.

EXPERIMENTAL EXAMPLE 6

Tertiary hydrolysis pH and temperature vs. degree of coloration

The material solution was treated under the conditions listed in Table 1, except that the hydrolyzate resulting from the primary autoclaving was adjusted to varying pH values and then subjected to tertiary hydrolysis at varying temperatures. The degree of coloration and DE of the refined concentrates obtained were determined with the results given in Tables 8 and 9.

TABLE 8

| pH | 75° C. | 80° C. | 85° C. | 90° C. | 95° C. | 100° C. |
|---|---|---|---|---|---|---|
| 5.0 | 1.04 | 0.95 | 1.02 | 1.17 | 1.31 | 1.50 |
| 5.5 | 1.33 | 1.05 | 1.10 | 1.34 | 1.47 | 1.66 |
| 6.0 | 1.42 | 1.31 | 1.11 | 1.30 | 1.65 | 1.68 |
| 6.5 | 1.37 | 1.22 | 1.32 | 1.51 | 1.58 | 1.94 |
| 7.0 | 1.68 | 1.95 | 1.84 | 1.88 | 2.04 | 2.72 |
| 7.5 | 1.82 | 2.03 | 1.96 | 2.11 | 2.87 | 3.16 |

TABLE 9

| pH | 75° C. | 80° C. | 85° C. | 90° C. | 95° C. | 100° C. |
|---|---|---|---|---|---|---|
| 5.0 | 8.53 | 9.64 | 9.74 | 9.93 | 10.77 | 10.87 |
| 5.5 | 8.68 | 9.91 | 10.03 | 10.45 | 10.92 | 11.42 |
| 6.0 | 8.82 | 10.02 | 10.22 | 10.98 | 11.13 | 11.53 |
| 6.5 | 8.90 | 10.34 | 10.53 | 11.21 | 11.45 | 11.60 |
| 7.0 | 8.94 | 10.48 | 10.67 | 11.22 | 11.51 | 12.04 |
| 7.5 | 8.98 | 10.52 | 10.88 | 11.35 | 11.62 | 12.11 |

Remarkable coloration was observed when the pH was at least 7 or the temperature was not lower than 95° C. Although the degree of coloration was low at a pH of 5 or at a temperature of 75° C., the DE value then measured indicated a low hydrolysis velocity. Most preferably, therefore, the pH is 5.5 to 6.5, and the temperature is 80° to 90° C.

EXPERIMENTAL EXAMPLE 7

Secondary Autoclaving pH and Time Vs. Rate of Filtration

The material solution was treated under the conditions listed in Table 1, except that the hydrolyzate resulting from the tertiary hydrolysis was adjusted to varying pH values and then secondarily autoclaved for varying periods of time. The hydrolyzates thus treated were adjusted to a concentration of 30% and filtered to determine the rate of filtration before refining. Table 10 shows the result.

TABLE 10

| time | pH | | | | | |
|---|---|---|---|---|---|---|
| | 3.5 | 4.0 | 5.0 | 5.5 | 6.5 | 7.0 |
| 1 min. | 8.4 | 10.2 | 8.1 | 6.4 | 3.5 | 3.7 |
| 3 | 10.7 | 14.6 | 15.8 | 9.1 | 4.3 | 4.0 |
| 5 | 9.6 | 21.2 | 21.6 | 10.7 | 5.8 | 5.9 |
| 10 | 11.2 | 29.7 | 27.3 | 12.4 | 6.4 | 4.9 |
| 15 | 13.1 | 32.7 | 30.6 | 11.8 | 7.0 | 6.1 |

EXPERIMENTAL EXAMPLE 8

Secondary Autoclaving pH and Temperature Vs. Degree of Coloration

The material solution was similarly treated under the conditions listed in Table 1, except that the hydrolyzate obtained by the tertiary hydrolysis was adjusted to varying pH values and then secondarily autoclaved at varying temperatures. The resulting hydrolyzates were checked for degree of coloration with the result given in Table 11.

TABLE 11

| pH | Temp. | | | | | |
|---|---|---|---|---|---|---|
| | 105° C. | 115° C. | 125° C. | 135° C. | 140° C. | 150° C. |
| 3.5 | 0.79 | 0.86 | 0.91 | 0.99 | 1.21 | 1.48 |
| 4.0 | 0.80 | 0.84 | 0.98 | 1.03 | 1.33 | 1.50 |
| 5.0 | 0.83 | 1.09 | 1.11 | 1.42 | 1.56 | 1.68 |
| 5.5 | 1.14 | 1.28 | 1.51 | 1.63 | 1.63 | 1.96 |
| 6.0 | 1.61 | 1.64 | 1.84 | 2.16 | 2.16 | 2.98 |

Tables 10 and 11, showing the conditions for the secondary autoclaving and the result obtained, reveal that the filtration rate was low at a pH of 3.5, and at pH values of 5.5 or higher, or was low when the time was 1 minute and remained unchanged when the time exceeded 10 minutes. Coloration became evident at a pH of over 5 or a temperature of over 135° C., and remained unchanged at a pH of below 5 or at a temperature of below 115° C. Ideally, therefore, the temperature is 115° to 135° C., the pH is 4.0 to 5.0, and the time is 3 to 10 minutes.

EXPERIMENTAL EXAMPLE 9

Difference due to different alpha-amylases

The material solution was treated under the conditions given in Table 1 using alpha-amylase derived from *B. licheniformis* or Kleistase KD (product of Daiwa Kasei Co., Ltd.). alpha-amylase derived from *B. subtilis*, for comparison. The refined concentrates obtained were checked for the degree of coloration, turbidity, and the indigestible dextrin, content which is an important characteristic of the products of the invention. Table 12 shows the result.

TABLE 12

| Alpha-amylase | Degree of coloration | Turbidity | Indigestible dextrin content |
|---|---|---|---|
| B. licheniformis | 1.11 | 0.020 | 56.7% |
| B. subtilis | 1.34 | 0.031 | 48.5% |

EXPERIMENTAL EXAMPLE 10

Rate of Filtration and Quality in the Case Where One of the Processes was Omitted The material solution was treated under the conditions given in Table 1 without conducting one of the process listed in Table 1. Table 13 shows the result of analysis of the refined concentrates, and the amount of precipitate produced when the concentrates, as added to the orange juice, were allowed to stand in a refrigerator at 2° C. for 10 days. For comparison, Table 13 also shows the corresponding results achieved when all process were performed.

TABLE 13

| Omitted process | Rate of filtration | Turbidity | Coloration | Amt. of precipitate |
|---|---|---|---|---|
| Primary hydrolysis | 23.8 | 0.065 | 1.41 | 14.0 |
| Secondary hydrolysis | 17.3 | 0.143 | 1.26 | 3.8 |
| Primary autoclaving | 25.5 | 0.182 | 1.18 | 4.8 |
| Tertiary hydrolysis | 21.4 | 0.104 | 1.21 | 3.0 |
| Secondary autoclaving | 3.4 | 0.142 | 1.11 | 3.4 |
| None | 27.3 | 0.020 | 1.11 | 2.6 |

When one of the five processes was omitted, a lower filtration rate and greater turbidity, degree of coloration and amount of precipitate apparently resulted than when all the steps were performed.

EXAMPLES

The present invention will be described in greater detail with reference to the following examples.

EXAMPLE 1

Using pressurized air, 2.5 liters of 1% solution of hydrochloric acid was sprayed onto 25 kg of commercial potato starch placed in a ribbon mixer while rotating the mixer, with the mixture then passed through a disintegrator to obtain a uniform mixture, and thereafter aged in the ribbon mixer for 10 hours. The mixture was pre-dried to a water content of about 3% by a flash dryer, subsequently continuously charged into a converter of the rotary kiln type and heat-treated at 180° C. for 2 hours to obtain about 21 kg of pyrodextrin.

A 30 liter quantity of water was added to 20 kg of the pyrodextrin to prepare a solution, and the solution was adjusted to a pH of 7.8 with 20% aqueous solution of sodium hydroxide and subjected to primary hydrolysis at 30° C. for 14 hours with 40 g of alpha-amylase (TERMAMYL 120 L, product of Novo Industry Co., Ltd.) added to the solution. The hydrolyzate was then placed into an autoclave, heated to 88° C. and subjected to secondary hydrolysis for 40 minutes. Subsequently, steam was charged into the autoclave. When the internal temperature reached 130° C., the hydrolyzate was maintained at this temperature for 8 minutes for primary autoclaving. The hydrolyzate was discharged into a tank, cooled to 85° C. and thereafter subjected to tertiary hydrolysis for 15 minutes with 20 g of the same alpha-amylase. The hydrolyzate was sent into the autoclave, treated for secondary autoclaving in the same manner as in the primary autoclaving, discharged, cooled to about 80° C., thereafter decolorized with activated carbon, filtered and desalted with ion exchange resin for refining. The resulting hydrolyzate was spray-dried by a spray dryer to obtain about 18 kg of a powder of pyrodextrin hydrolyzate.

EXAMPLE 2

Using pressurized air, 2.5 liters of 1% solution of hydrochloric acid was sprayed into 25 kg of commercial corn starch placed in a ribbon mixer while rotating the mixer, with the mixture then passed through a disintegrator to obtain a uniform mixture, and thereafter aged in the ribbon mixer for 10 hours. The mixture was pre-dried to a water content of about 3% by a flash dryer, subsequently continuously charged into a converter of the rotary kiln type and heat-treated at 150° C. for 3 hours to obtain about 21 kg of pyrodextrin.

A 26 liter quantity of water was added to 20 kg of the pyrodextrin to prepare a solution, and the solution was adjusted to a pH of 7.6 with 20% aqueous solution of sodium hydroxide and subjected to primary hydrolysis at 30° C. for 6 hours with 30 g of alpha-amylase (TERMAMYL 120 L, product of Novo Industry Co., Ltd.) added to the solution. The hydrolyzate was then placed into an autoclave, heated to 82° C. and subjected to secondary hydrolysis for 25 minutes. Subsequently, steam was charged into the autoclave. When the internal temperature reached 125° C., the hydrolyzate was maintained at this temperature for 10 minutes for primary autoclaving. The hydrolyzate was discharged into a tank, cooled to 86° C and thereafter subjected to tertiary hydrolysis for 35 minutes with 20 g of the same alpha-amylase. The hydrolyzate was sent into the autoclave, treated for secondary autoclaving in the same manner as in the primary autoclaving, discharged, cooled to about 80° C., thereafter decolorized with activated carbon, filtered and desalted with ion exchange resin for refining. The resulting hydrolyzate was spray-dried by a spray dryer to obtain 17 kg of a powder of pyrodextrin hydrolyzate.

EXAMPLE 3

Using Pressurized air, 15 liters of 1% solution of hydrochloric acid was sprayed onto 300 kg of commercial corn starch placed in a ribbon mixer while rotating the mixer, with the mixture then passed through a disintegrator to obtain a uniform mixture, and further treated in the ribbon mixer for 1 hour. The mixture was pre-dried to a water content of about 8% by a flash dryer, subsequently continuously charged into a twin-screw extruder (Model TEX-52FSS-20AW-V, product of Japan Steel Works, Ltd.) and heat-treated under the following conditions to obtain about 250 kg of pyrodextrin.

| | |
|---|---|
| Speed of rotation | 150 r.p.m. |
| Inlet temperature | room temperature (about 20° C.) |
| Maximum temperature | 170° C. |
| Discharge temperature (of extrudate) | 130° C. |
| Residence time (reaction time) | 9 sec. |

A 40 liter quantity of water was added to 20 kg of the pyrodextrin to prepare a solution, and the solution was adjusted to a pH of 8.4 with 20% aqueous solution of sodium hydroxide and subjected to primary hydrolysis at 30° C. for 18 hours with 30 g of alpha-amylase (TERMAMYL 120 L, product of Novo Industry Co., Ltd.) added to the solution. The hydrolyzate was then placed into an autoclave, heated to 86° C. and subjected to secondary hydrolysis for 30 minutes. Subsequently, steam was charged into the autoclave. When the internal temperature reached 135° C., the hydrolyzate was maintained at this temperature for 3 minutes for primary autoclaving. The hydrolyzate was discharged into a tank, cooled to 82° C. and thereafter subjected to tertiary hydrolysis for 20 minutes with 20 kg of the same alpha-amylase. The hydrolyzate was sent into the autoclave, treated for secondary autoclaving in the same manner as in the primary autoclaving, discharged, cooled to about 80° C., thereafter decolorized with activated carbon, filtered and desalted with ion exchange resin for refining. The resulting hydrolyzate was spray-dried by a spray dryer to obtain about 18 kg of a powder of pyrodextrin hydrolyzate. Table 14 shows the properties determined of the products obtained in Examples 1 to 3.

TABLE 14

| Example | Rate of filtration | Turbidity | Coloration | Amt. of precipitate |
|---|---|---|---|---|
| 1 | 29.7 | 0.021 | 1.06 | 2.8 |
| 2 | 25.8 | 0.024 | 0.95 | 2.6 |
| 3 | 28.6 | 0.020 | 0.87 | 2.2 |

What we claim is:

1. A process for preparing a pyrodextrin hydrolysate by enzymatic hydrolysis which comprises the steps of:
   (a) providing pyrodextrin which is prepared by heating starch in the presence of hydrochloric acid,
   (b) dissolving the pyrodextrin in water,
   (c) adjusting the aqueous solution of pyrodextrin to a pH of from 7.0 to 8.5,
   (d) pre-hydrolyzing the pH adjusted solution with alpha-amylase produced by *Bacillus licheniformis* at a temperature of from 20° to 40° C. for 6 to 20 hour to obtain a hydrolysate,
   (e) adjusting the hydrolysate to a pH of from 5.5 to 6.5,
   (f) hydrolyzing the pH adjusted hydrolysate with said alpha-amylase at a temperature from 80° to 90° C.,
   (g) adjusting the hydrolysate to a pH of from 4.0 to 5.0,
   (h) autoclaving the resulting hydrolysate at a temperature of from 115° to 135° C. for 3 to 10 minutes,
   (i) hydrolyzing the autoclaved hydrolysate with said alpha-amylase at a temperature of from 80° to 90° C.,
   (j) adjusting the hydrolysate to a pH of from 4.0 to 5.0, and
   (k) autoclaving the resulting hydrolysate at a temperature of from 115° to 135° C. for 3 to 10 minutes.

2. The process of claim 1, wherein said alpha-amylase is used in an amount of 0.05 to 0.2% by weight based on the weight of the pyrodextrin.

3. The process of claim 1, wherein the pH adjusted hydrolysate is hydrolyzed in step (f) with said alpha-amylase so that it is hydrolyzed to 30 to 60% of the DE value of the final product.

4. The process of claim 1, wherein the hydrolysate obtained in step (k) is then decolorized with activated carbon, filtered, desalted, and decolorized with an ion exchange resin.

* * * * *